United States Patent
Yamamoto

(10) Patent No.: US 7,771,820 B2
(45) Date of Patent: Aug. 10, 2010

(54) MONOCRYSTAL, NANO WIRE MATERIAL, ELECTRONIC ELEMENT, AND METHOD OF PRODUCING NANO WIRE MATERIAL

(75) Inventor: Hiroshi Yamamoto, Tokyo (JP)

(73) Assignee: Japan Science and Technology Agency, Kawaguchi-Shi (JP)

(*) Notice: Subject to any disclaimer, the term of this patent is extended or adjusted under 35 U.S.C. 154(b) by 293 days.

(21) Appl. No.: 11/629,904

(22) PCT Filed: Jun. 15, 2005

(86) PCT No.: PCT/JP2005/011393

§ 371 (c)(1), (2), (4) Date: Oct. 3, 2007

(87) PCT Pub. No.: WO2005/123637

PCT Pub. Date: Dec. 29, 2005

(65) Prior Publication Data

US 2008/0124545 A1    May 29, 2008

(30) Foreign Application Priority Data

Jun. 17, 2004   (JP) ............................. 2004-179175

(51) Int. Cl.
*D02G 3/00* (2006.01)
*H01B 1/00* (2006.01)

(52) U.S. Cl. .................... 428/401; 252/500; 174/110 A
(58) Field of Classification Search .................. 428/401
See application file for complete search history.

(56) References Cited

U.S. PATENT DOCUMENTS

| 6,208,553 | B1* | 3/2001 | Gryko et al. | 365/151 |
| 7,317,047 | B2* | 1/2008 | Hsu | 524/165 |
| 2002/0040805 | A1* | 4/2002 | Swager | 174/110 A |
| 2004/0235184 | A1* | 11/2004 | Swager | 436/149 |

OTHER PUBLICATIONS

U. Klabunde et al., Journal of the American Chemical Society, 1974, vol. 96, No. 23, pp. 7376 to 7378.
R. Kato et al., Synthetic Metals, 1993, vol. 56, No. 1, pp. 2084 to 2089.

* cited by examiner

*Primary Examiner*—D. Lawrence Tarazano
*Assistant Examiner*—Altrev C Sykes
(74) *Attorney, Agent, or Firm*—Birch, Stewart, Kolasch & Birch, LLP

(57) ABSTRACT

A crystalline nano wire material which can be used as a nano-level wire is provided.

A molecular monocrystal having a high anisotropy for electrical resistivity is used.

24 Claims, 4 Drawing Sheets

(a)

(b)

MONOCRYSTAL, NANO WIRE MATERIAL, ELECTRONIC ELEMENT, AND METHOD OF PRODUCING NANO WIRE MATERIAL

TECHNICAL FIELD

The present invention relates to a nano wire material usable for a nano-level electronic element, a monocrystal used therein, an electronic element comprising the nano wire material, and a method of producing the nano wire material.

BACKGROUND ART

With recent brilliant advancement in electronics, a variety of nano wire materials have been studied. Nano wire materials currently used in the field of electronics designed for wiring in a two-dimensional plane. For example, an electron beam lithography, a multi-layered circuit technology based thereon, an integrated circuit technology using an SAM (Self-Assembled Monolayer) are known (Okawa, Yuji; Aono, Masakazu, Nature, 409, 683-684 (2001)). However, the wiring technology in a two-dimensional plane has a restriction in integration density of elements even with any increase in dimension of patterns.

In a known fine fabrication technology, since light or electron beams need to be irradiated to a plane substrate, a space for transmitting light or substances is required and only one circuit layer can be drawn one process.

On the other hand, H. R. Zeller et al. J. Phys. Chem. Solids, 35, 77 (1974) discloses a technology of producing a nano-level wire having three-dimensional periodicity by crystallization. However, since it is impossible to control the performance of an insulating portion and the relative arrangement of wires, it can hardly be used as a nano wire.

DISCLOSURE OF THE INVENTION

The present invention is contrived to solve the above-mentioned problem. An object of the invention is to provide a crystalline nano wire material which can be used as a nano-level wire.

In this condition, as a result of the inventor's eager study, the above-mentioned object can be accomplished using super molecules obtainable by integrating weak reversible interactions acting between molecules and organizing the molecules into a regulated collection. That is, the present invention is completed by using crystals in which an insulating portion (an insulating coating of a wire) having an insulating property still higher than that in the past is covered on the surface of a conductive portion. By the use of such means, a nano wire material according to the invention is obtained without synthesizing complicated compounds. Specifically, the invention is accomplished by the following means:

1. A molecular monocrystal having a high anisotropy for electrical resistivity.

2. A molecular monocrystal comprising a conductive portion and an insulating portion covering the conductive portion, wherein the conductive portion comprises conductive molecules which are arranged in series, the insulating potion comprises insulating molecules, the resistivity of the insulating portion is larger by 100,000 times or more than the resistivity of the conductive portion, the conductive molecules are any one selected from the group consisting of cation radical salts, anion radical salts, organic metal complexes, and chalcogen-containing organic compounds, and the insulating molecules contain an aromatic ring and a halogen atom.

3. A molecular monocrystal comprising a conductive portion and an insulating portion covering the conductive portion, wherein the resistivity of the insulating portion is larger by 100,000 times or more than the resistivity of the conductive portion, 1 to 16 lines in which conductive molecules having a molecular weight in the range of 150 to 800 are arranged in series are arranged in parallel in the conductive portion, the insulating portion comprises insulating molecules having a molecular weight in the range of 500 to 10,000, and the molecular monocrystal is obtainable by electrolysis of a solution containing the conductive molecules and the insulating molecules.

4. A nano wire material having a monocrystalline supramolecular architecture which comprises a conductive portion and an insulating portion covering the conductive portion, wherein the conductive portion comprises conductive molecules which are arranged in series, the insulating portion comprises insulating molecules, and the resistivity of the insulating portion is larger by 100,000 times or more than the resistivity of the conductive portion.

5. A nano wire material comprising a monocrystal which comprises a conductive portion and an insulating portion covering the conductive portion, wherein the resistivity of the insulating portion is larger by 100,000 times or more than the resistivity of the conductive portion, 1 to 16 lines in which conductive molecules having a molecular weight in the range of 150 to 800 are arranged in series are arranged in parallel in the conductive portion, the insulating portion comprises insulating molecules having a molecular weight in the range of 500 to 10,000, and the monocrystal is obtainable by electrolysis of a solution containing the conductive molecules and the insulating molecules.

6. The nano wire material according to 4 or 5, wherein the conductive molecules are any one selected from the group consisting of cation radical salts, anion radical salts, organic metal complexes, and chalcogen-containing organic compounds.

7. A nano wire material comprising a monocrystal which has a conductive portion and an insulating portion covering the conductive portion, wherein the conductive portion comprises conductive molecules which are arranged in series and the insulating portion comprises insulating molecules, the resistivity of the insulating portion is larger by 100,000 times or more than the resistivity of the conductive portion, the conductive molecules are any one selected from the group consisting of cation radical salts, anion radical salts, organic metal complexes, and chalcogen-containing organic compounds, and the insulating portion contains an organic molecule.

8. The nano wire material according to any one of 4 to 7, wherein the insulating molecules contain a benzene ring and a halogen atom.

9. The nano wire material according to any one of 5 to 8, wherein the monocrystal has a supramolecular architecture.

10. The nano wire material according to any one of 4 to 9, wherein the conductive molecules have a fulvalene skeleton.

11. The nano wire material according to 10, wherein the conductive molecules are tetraselenafulvalene.

12. The nano wire material according to any one of 4 to 11, wherein the insulating molecules have an aromatic-series skeleton.

13. The nano wire material according to 12, wherein the insulating molecules are an aromatic series having an alkynyl group.

14. The nano wire material according to any one of 4 to 13, wherein the insulating molecules contain a halogen atom.

15. The nano wire material according to 14, wherein the insulating molecules are bonded to each other with the halogen atom therebetween.

16. The nano wire material according to any one of 4 to 15, wherein the insulating molecules have a twofold symmetry.

17. The nano wire material according to any one of 4 to 16, wherein two or more of the conductive portions are collected to be covered with the insulating portion.

18. The nano wire material according to any one of 4 to 17, wherein the nano wire material comprises a first layer comprising the conductive portion which are arranged in parallel and a second layer comprising the conductive portion which are arranged in parallel, and the second layer is stacked on the first layer so that the conductive portion of the first layer is approximately perpendicular to the conductive portion of the second layer.

19. The nano wire material according to 18, wherein the first layer(s) and the second layer(s) are stacked alternatively.

20. The nano wire material according to any one of 4 to 19, wherein the resistivity of the insulating portion is larger by 10,000,000 times or more than the resistivity of the conductive portion.

21. The nano wire material according to any one of 4 to 20, wherein the thickness of the insulating portion is 1.0 nm or more.

22. An electronic element comprising the nano wire material according to any one of 4 to 21.

23. A method of producing the nano wire material according to any one of 4 to 21, comprising forming a supramolecular architecture out of a solution containing conductive molecules and insulating molecules by the use of interaction between the molecules.

BRIEF DESCRIPTION OF THE DRAWINGS

In FIG. 1, reference numeral 1 denotes a conductive portion, reference numeral 2 denotes an insulating portion, reference numeral 3 denotes a conductive molecule, and reference numeral 4 denotes an insulating molecule.

In FIG. 3, reference numeral 1 denotes a conductive portion and reference numeral 2 denotes an insulating portion.

DETAILED DESCRIPTION OF THE INVENTION

Figure 1:
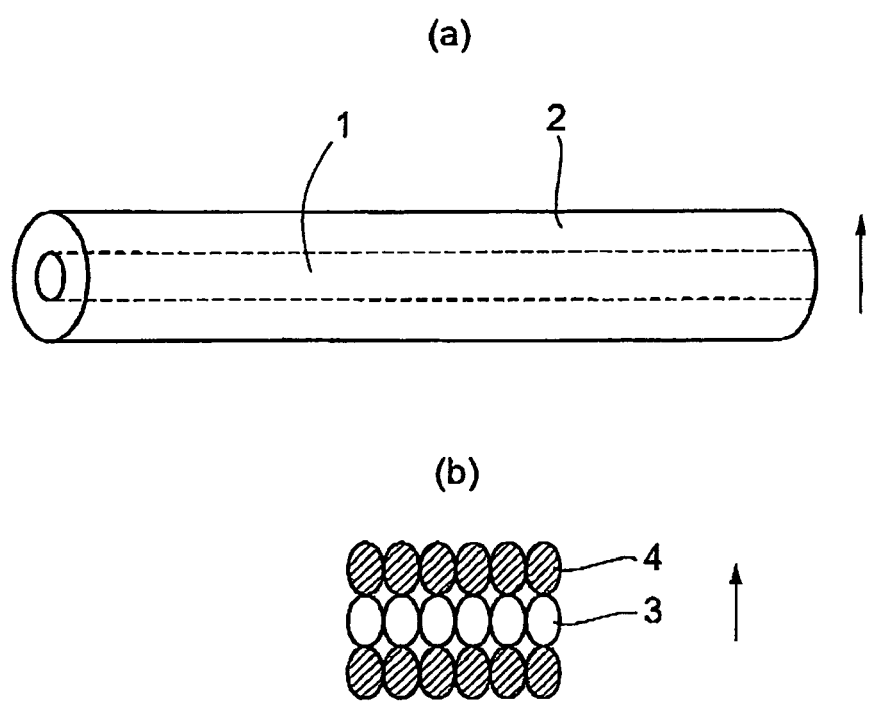
FIG. 1 is a conceptual diagram illustrating a first embodiment of the invention.

Hereinafter, the present invention will be described in detail. In the following description, "~" is used as a meaning including the numerals described before and after it as the upper limit value and the lower limit value. A molecule in the following description means a chemically stable collection of atoms in which one or more atoms are bonded to each other by a covalent bond, and contains a single-atom molecule such as halide ions.

(1) Conductive Molecule

In the present invention, conductive molecules are arranged in series and the arrangement is not particularly limited as long as the conductive molecule arranged in series can be arranged again in parallel as needed. In the present invention, it is very important that the conductive molecules are arranged with regularity in a macro scale. Since the conductive molecule can be arranged in parallel with regularity, an insulating portion covering the conductive molecule can be provided using, for example, a supramolecular theory, thereby obtaining a monocrystal with a dense configuration and a nano wire material with a dense configuration according to the invention.

Specifically, it is preferable that the conductive molecule according to the invention are one selected from the group consisting of cation radical salts, anion radical salts, organic metal complexes, and chalcogen-containing organic compounds. The molecular weight of the conductive molecule used in the invention is not particularly limited so long as they can constitute a crystal according to the invention and is preferably in the range of 150 to 800. The resistivity of the conductive molecule used in the invention is preferably $10^5$ $\Omega$cm or less and more preferably 1 $\Omega$cm or less.

(1-1) Cation Radical Salts

It is preferable that the cation radical salt according to the invention is obtained by oxidizing donor molecules. The donor molecules are not particularly limited so long as they do not depart from the gist of the invention. As the donor molecules, a compound having a fulvalene skeleton and a compound having a phenylene skeleton can be preferably used, the compound having a fulvalene skeleton is more preferably used, and tetraselenafulvalene is still more preferably used.

(1-2) Anion Radical Salts

It is preferable that the anion radical salt according to the invention is obtained by reducing acceptor molecules or partially oxidizing anion metal complexes. Among these, it is preferable that the anion radical salt is obtained by reducing the acceptor molecules.

The acceptor molecules according to the invention are not particularly limited so long as they do not depart from the gist of the invention and 7,7,8,8-tetracyanoquinodimethane (TCNQ), dicyanoquinone diimine (DCNQI) and a variety of quinoide (such as Chloranil) are preferably used and 7,7,8,8-tetracyanoquinodimethane (TCNQ) and dicyanoquinone diimine (DCNQI) are more preferably used.

On the other hand, the anion metal complexes are not particularly limited so long as they do not depart from the gist of the invention and a compound $(M(dmit)_2)$ (wherein M is Ni, Pd, or Pt) having a dithiolene metal skeleton, $M(mnt)_2$ (wherein M is Ni, Pd, or Pt), and a phthalocynanine complex are preferable and the compound $(M(dmit)_2)$ (wherein M is Ni, Pd, or Pt) having a dithiolene metal skeleton is more preferable.

Compounds corresponding to the anion radical salts can be preferably used among the compounds exemplified in (1-1).

Charge migrating complexes between the acceptor molecules and the donor molecules exemplified in (1-1) can be preferably used.

(1-3) Organic Metal Complexes

It is preferable that the metal complex according to the invention is obtained by oxidizing anion metal complexes until they become neutral. The anion metal complexes usable herein are not particularly limited so long as they do not depart from the gist of the invention and widely known compounds may be used. A specific example thereof can include $Ni(tmdt)_2$.

Among the compounds exemplified in (1-1) and (1-2), compounds corresponding to metal complexes may be used.

(1-4) Chalcogen-Containing Organic Compounds

As the chalcogen-containing organic compounds according to the invention, organic compounds containing selenium atom or sulfur can be preferably used.

As the organic compounds containing selenium atoms, compounds having a ring shape can be preferably used and examples thereof can include compounds having a fulvalene skeleton and a pentalene skeleton. Among these, the compounds having a fulvalene skeleton can be preferably used.

As the organic compounds containing sulfur, compounds having a heterocyclic skeleton containing sulfur can be used preferably used and examples thereof can include compounds having a thiophene skeleton, a dithiophene skeleton, a thiazole skeleton, a thiane skeleton, and/or a dithiane skeleton. Preferable examples of the organic compounds containing sulfur according to the invention can include compounds having a tetrathiafulvalene (TTF) skeleton or compounds (M(tmdt)$_2$) (wherein M is Ni, Pd, or Pt) having a dithiolene metal skeleton. Preferable examples of the compounds having a tetrathiafulvalene (TTF) skeleton can include tetrathiafulvalene (TTF), ethylene dithio tetrathiafulvalene (EDT-TTF), and bis(ethylene dithio) tetrathiafulvalene (BEDT-TTF) and ethylene dithio tetrathiafulvalene (EDT-TTF) can be more preferably used.

Compounds corresponding to the chalcogen-containing organic compounds can be preferably used among the compounds exemplified in (1-1) to (1-3).

(2) Insulating Molecule

The insulating molecules according to the invention are not particularly limited so long as they do not depart from the gist of the invention, preferable examples thereof can include molecules containing a double bond of carbon-carbon and a halogen atom and molecules containing an aromatic ring (more preferably benzene ring) and a halogen atom.

The molecular weight of the insulating molecules used in the invention is not particularly limited so long as it can constitute the crystal according to the invention, but is preferably in the range of 300 to 3,000. The resistivity of the insulating molecules used in the invention is preferably $10^{10}$ Ωcm or more and more preferably $10^{13}$ Ωcm or more.

Ethylene can be preferably used as the double bond of carbon-carbon contained in the insulating molecule according to the invention. A molecule having a chain having a double bond of carbon-carbon as a main chain and having a hydrogen atom replaced with a halogen atom is used preferably as the molecules containing the double bond of carbon-carbon and the halogen atom according to the invention. As the halogen atom, a fluorine atom, a chlorine atom, a bromine atom and/or an iodine atom are used preferably and a fluorine atom and/or an iodine atom are more preferably used.

As the benzene ring contained in the molecule containing a benzene ring and a halogen, only one benzene ring or a compound of two or more benzene rings bonded through one or two or more single bond can be preferably used atom and a compound having a biphenyl skeleton is more preferably used. The number of carbons of the benzene ring is preferably 20 or more and more preferably in the range of 20 to 80.

As the halogen atom, a fluorine atom, a chlorine atom, a bromine atom and/or an iodine atom are preferably used and a fluorine atom and/or an iodine atom are more preferably used.

The molecule containing a benzene ring and a halogen atom according to the invention has preferably a triple bond and more preferably a triple bond of carbon-carbon. Specifically, a molecule having a triple bond of carbon-carbon is preferably used as a substituent group of the benzene ring (or a skeleton portion including the benzene ring). As the substituent group, an alkynyl group is preferably used and an ethynyl group is more preferably used. The alkynyl group is further preferably replaced with a halogen atom.

The insulating molecule according to the invention preferably use a molecule satisfying any one of a compound having a triple bond and a biphenyl skeleton, an organic compound having the number of carbons of 20 or more, a compound contain fluorine, a compound having a twofold symmetry, and a compound having a strong intermolecular action among compounds having an aromatic ring (more preferably, a benzene ring) and a halogen atom. Alkynyl biphenyl halide, amide, and carboxyl acid can be preferably used as the insulating molecule and specific examples thereof can include 2,2',4,4',6,6'-hexafluoro-3,3',5,5'-tetraiodethynylbiphenyl and 2,2',6,6'-tetramethyl-4,4'-dihydroxycarbonyl-3,3',5,5'-tetrakisiodethynylbiphenyl.

(3) Monocrystal Comprising Conductive Molecule and Insulating Molecule (3-1) The monocrystal according to the invention is a molecular monocrystal having a high anisotropy for electrical resistivity. Here, the high anisotropy means that the ratio of electrical resistivities in direction perpendicular to each other is preferably 100,000 times and more preferably $10^7$ times or more.

More specifically, the monocrystal has a conductive portion comprising conductive molecules arranged in series, and an insulating portion comprising insulating molecules and covering the conductive portion. The resistivity of the insulating portion is larger by 100,000 times than that of the conductive portion.

A preferably combination of conductive molecules and insulating molecules is not particularly limited so long as it satisfies the above-mentioned requirement and preferably examples thereof can include a combination of a conductive molecule having resistivity in the range of $10^{-5}$ Ωcm to $10^0$ Ωcm and an insulating molecule having resistivity in the range of $10^8$ Ωcm to $10^{15}$ Ωcm and/or a combination of a conductive molecule having a molecular weight in the range of 150 to 800 and an insulating molecule having a molecular weight in the range of 500 to 10,000.

In the crystal according to the invention, the insulating molecules are bonded through a halogen atom, the halogen atom is preferably bonded through one of a bromine atom and an iodine atom, and the halogen atom is more preferably bonded through at least an iodine atom. The halogen atom is contained in the insulating molecules.

The composition ratio (mol %) of the conductive molecule and the insulating molecule in the crystal according to the invention is preferably in the range of 10~90:90~10 and more preferably in the range of 20~70:80~30. The molecules according to the invention may include molecules (or atoms) not belonging to any of the conductive molecules and the insulating molecules described in the invention. In this case, the molecules (or atoms) occupy 50 mol % or less of the entire crystal.

The crystal according to the invention has a crystalline property enough to be used for the nano wire material and may include a crystal having a non-complete periodicity in such a range. The crystal according to the invention is preferably a supramolecular architecture.

It is preferable that the nano wire material according to the invention comprises a monocrystal and has a supramolecular architecture.

The thickness of the insulating portion according to the invention is preferably 1.0 nm or more. By setting such a range, the leaking current between wires can be reduced to a negligible amount.

(3-2) Method of Manufacturing Nano Wire Material According to the Invention

The nano wire material according to the invention can be produced, for example, by applying a supramolecular theory. Specifically, in the nano wire material according to the invention, a technique of automatically making a wire-shaped structure at the time of crystallizing constituent molecules can be used by the use of a concept of self-organization of molecules or crystal engineering. That is, molecules constituting the insulating portion and conductive molecules constituting the conductive portion are strongly bonded to each other by a non-valent bond (such as a halogen bond). That is, this is different from the simple crystallization of one-dimensional wire such as a platinum complex known in the past. In the invention, since the molecular structure can be designed, the insulating portion can be thicker, the conductive portion can be thicker, or the relative arrangement of the wire can be controlled.

For example, the nano wire material can be produced by using the method described in the Report of Bulletin of the ETL, vol. 56, 4 number, page 6.

As a method of producing a crystal as used in the invention, a method of electrolyzing a solution, which is obtained by dissolving in the solvent containing the conductive molecules and the insulating molecules, and the other molecules as needed, on electrodes can be preferably used.

Preferable examples of other molecules can include halide ions and dibromoaurate, and chloride ions (such as tetraphenyl phosphonium chloride) are more preferable.

The solvent used for the electrolysis is not particularly limited so long as it does not depart from the gist of the invention, but preferable examples thereof can include ethanol, methanol, chlorobenzene, dichlorobenzene, and a mixed solution thereof.

The electrolysis can be performed by applying a voltage across the electrodes and the voltage for the electrolysis is preferably in the range of 1 to 25V.

The materials of the electrodes used for the electrolysis are not particularly limited, but preferably examples thereof can include gold (Au), titanium (Ti), chromium (Cr), tantalum (Ta), copper (Cu), aluminum (Al), molybdenum (Mo), tungsten (W), nickel (Ni), palladium (Pd), platinum (Pt), silver (Ag), tin (Sn), and combinations thereof.

(4) Nano Wire Material

Hereinafter, preferable embodiments of the nano wire material according to the invention will be described. FIG. 1(a) is a conceptual diagram illustrating a preferred embodiment of the nano wire material according to the invention, where reference numeral 1 denotes a conductive portion in which conductive molecules are arranged in series and reference numeral 2 denotes an insulating portion comprising insulating molecules and covering the conductive portion. Here, as shown in FIG. 1(b), in the first embodiment, the conductive molecules 3 are arranged in a wire shape and are surrounded with the insulating molecules. The conductive molecules and the insulating molecules are combined to form a crystal.

The nano wire material according to this configuration has a high conductivity in a direction in which the conductive molecules are arranged in series and has a high insulating property in a direction (arrow direction in FIG. 1) perpendicular to the direction. By using the crystal comprising the conductive molecules and the insulating molecules, it is possible to especially enhance the insulating property between the nano wire materials even when a number of nano wire materials are arranged as in a second embodiment to be described later. Since the nano wire material can be constituted as a crystal, the regularity is very excellent in controlling the relative arrangement between the nano wire materials.

Figure 2:
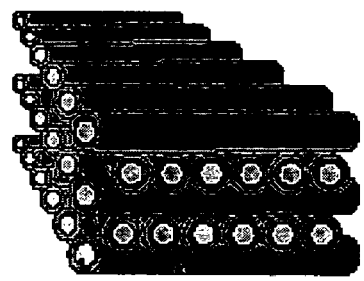
FIG. 2 is a conceptual diagram illustrating a second embodiment of the invention.
Figure 3:
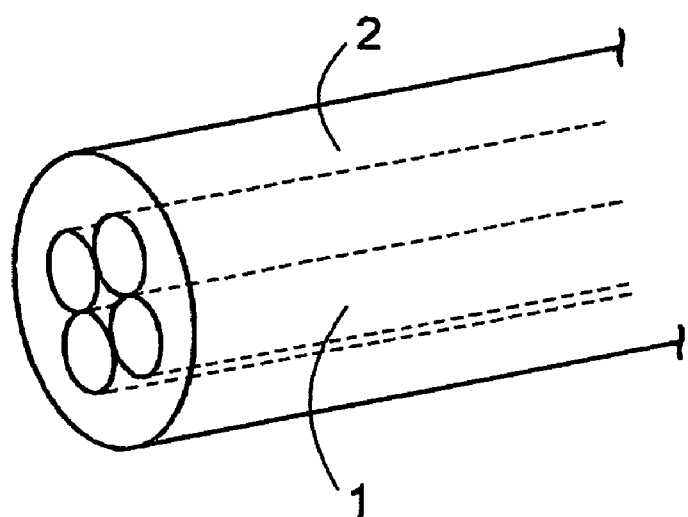
FIG. 3 is a conceptual diagram illustrating a third embodiment of the invention.

FIG. 2 is a conceptual diagram illustrating a nano wire material according to a second embodiment of the invention, where the nano wire materials according to the first embodiment are arranged in parallel to form a first layer, the nano wire material is stacked again perpendicular to the conductive portion of the nano wire material of the first layer to form a second layer, a nano wire material is stacked again perpendicular to the conductive portion of the nano wire material of the second layer as needed, and then a layer of the nano wire material is stacked. That is, the conductive portions of the nano wire materials of the layers are perpendicular to each other.

As in this embodiment, in order to arrange the nano wire materials to be perpendicular to each other, double symmetric molecules approximately perpendicular to each other may be used as the insulating molecules. Examples thereof can include the following compounds.

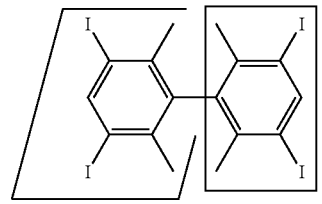

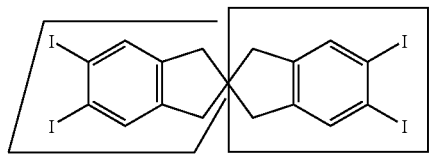

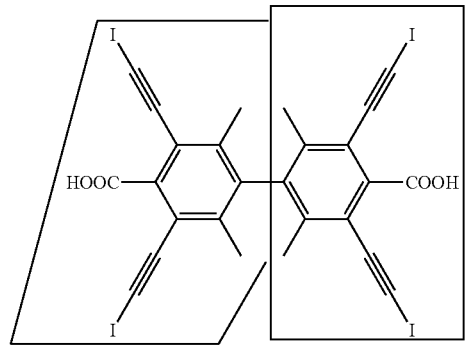

Here, the "approximately perpendicular" means "perpendicular" to such an extent that it can be used as an electronic element, but does not means that it is accurately perpendicular.

This configuration is possible to permit the nano wire material to serve as a wire of an electronic element.

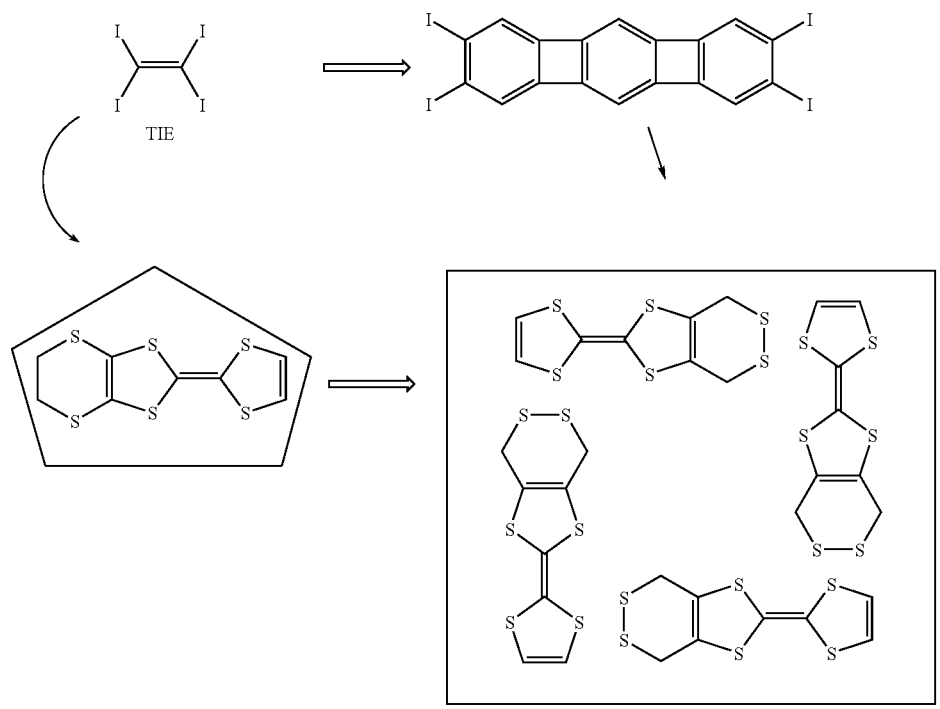

As opposed to, in the conductive portion of the first embodiment, the number of conductive molecule lines is one, in this embodiment, the number of conductive molecule lines is plural and hence it is possible to cope with the situation where a molecule line is broken off. The number of conductive molecule lines is preferably in the range of 2 to 16. The nano wire material according to this embodiment may be used to form the configuration according to the second embodiment.

In the invention, it is possible to easily perform a work of arbitrarily arranging the nano wire materials according to the first embodiment as the arrangement in the second embodiment or forming a contact between the nano wire materials. Since the conductive portion is not exposed, the short circuit due to contact between the conductive portions does not occur. That is, according to the invention, the molecules are regularly arranged in a large scale using a crystalline property, thereby the usability of the nano wire materials is enhanced.

The nano wire materials according to the invention may be arranged in a three-dimensional space. The nano wire material such as a carbon nano tube or the current semiconductor technologies are essentially based on a wiring in a two-dimensional plane and are not expanded to the three-dimensional space. On the contrary, in the invention, since the nano wire materials is arranged using periodicity of crystals, they can be three-dimensionally arranged. This has a considerable difference from the view of the number of elements contained in a unit volume. When the resolution of a wiring technology is 10,000 per dimension, elements of $10000^2$ bit (=$10^8$ bit, = 100 mega bit) can be arranged on a two-dimensional plane. However, elements of $10000^3$ bit (=$10^{12}$ bit, =1 tera bits) can be arranged in a three-dimensional space, thereby remarkably enhancing the number of elements. Therefore, the invention is extremely superior.

EXAMPLES

Hereinafter, the invention will be more specifically described with reference to examples. The materials, the amount of use, the ratios, the processing details, the processing order, and the like described in the following examples can be properly changed without departing from the gist of the invention. Accordingly, the scope of the invention is not limited to the specific examples described below.

(1) Tetraselenafulvalene (TSeF) was used as the conductive molecule, and 2,2',4,4',6,6'-hexafluoro-3,3',5,5'-tetraiodethynylbiphenyl (HFTIEB) was used as the insulating molecule.

(TSeF)Cl(HFTIEB) was used as the crystal. The crystal has a wire structure of a nano-meter scale (for example, a wire structure having a 1 nm thickness and 1 to 9 mm length) as the conductive molecule (TSeF) acts and the resistivity between the wires reaches $10^{13}$ Ωcm as the insulating molecule acts. Such an insulation performance amounts to a level of epoxy resin presently used in substrates of electronic products.

(2) Synthesis of TSeF Molecule

The synthesis of TSeF is performed on the basis of a method disclosed in E. M. Engler and V. V. Patel, J. Amer. Chem. Soc, vol. 96, 7376(1974).

(3) Synthesis of HFTIEB

The HFTIEB molecule was synthesized in accordance with the following synthesis path.

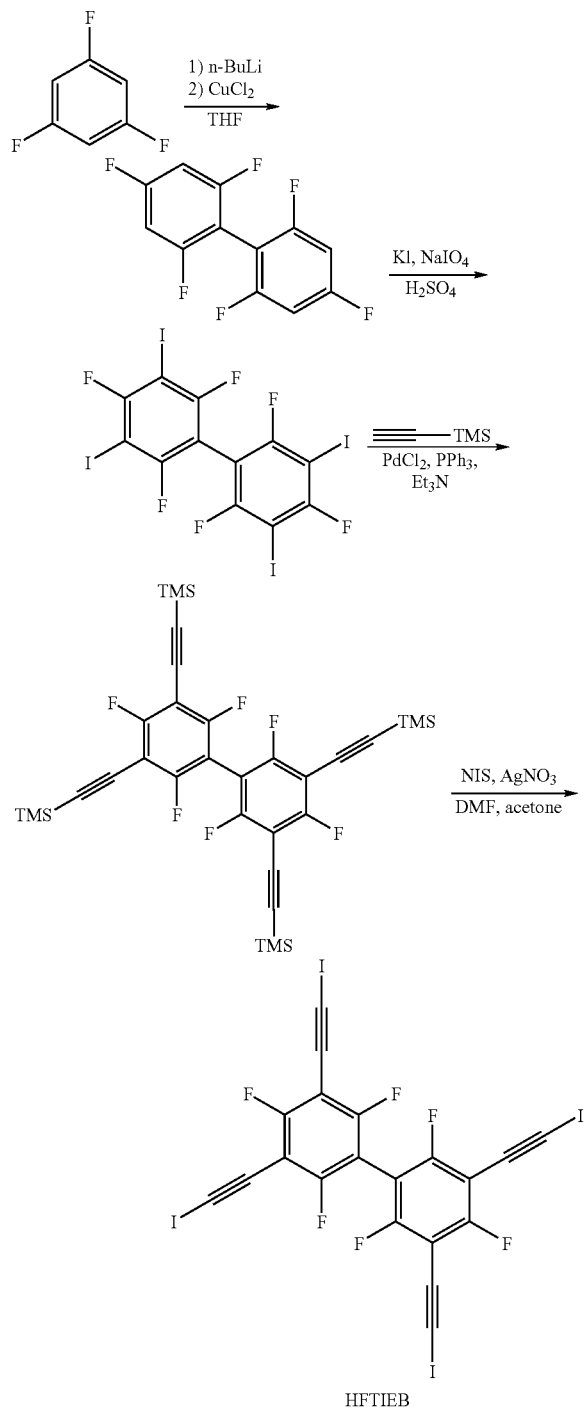

First, trifluorobenzene is reacted in the presence of tetrahydrofuran (THF) to obtain hexafluoro biphenyl, iodine is added in the presence of sulfuric acid, trimethylsilylacetylene is introduced so as to iodine-substitute trimethylsilyl group (TMS), thereby obtaining HFTIEB.

(4) Production of (TSeF)Cl(HFTIEB) Crystal 10 mg of TSeF, 20 mg of tetraphenyl phosphonium chloride, 80 mg of HFTIEB, 2 ml of methanol and 18 ml of chlorobenzene are added in an H-type cell, a constant current electrolysis was performed for 2 weeks using a platinum electrode. As a result, a monocrystal of (TSeF)Cl(HFTIEB) is developed on the positive electrode. The crystal structure was analyzed by X-ray diffraction. The lattice constants were Monoclinic, P2/a, Z=1, a=20.481, b=4.073, c=20.159 Å, = 108.75°, V=1592.4 Å$^3$, R=0.044, GOF=1.045.

Figure 4:
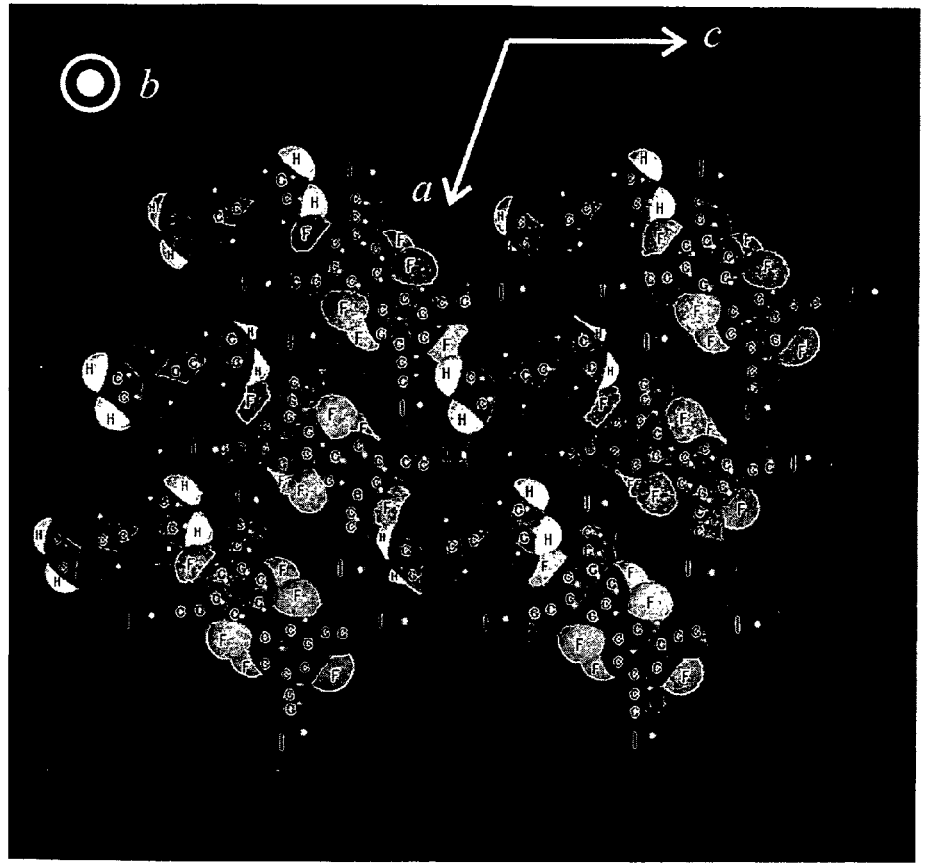
FIG. 4 shows a model of a crystal structure used by the embodiments.
Figure 4:
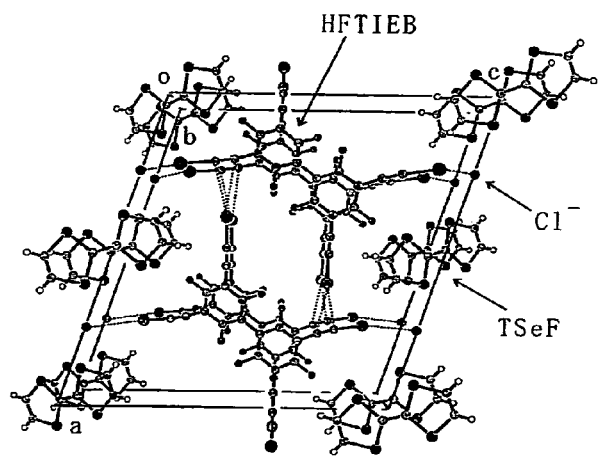

The crystal structure is shown in FIGS. 4(*a*) and 4(*b*). In FIG. 4(*b*), dotted lines represent a halogen bond.

(5) Measurement of Resistivity

In FIG. 4, the resistivity in b-axis direction was measured by the use of a general 4-terminal method. The resistivity in c-axis direction was measured mainly by the use of a 2-terminal method expect for surrounding either electrode with a guide electrode not to be affected by surface current. The measurement was performed by the use of a parameter analyzer (4200-SCS, manufactured by Keithley Instruments Inc.) and a special jig manufactured by Rockgate. Due to extremely high resistivity, the measurement was performed in a state that the capacitance of the sample is sufficiently saturated.

Low resistivity ($10^5$ Ωcm) was found in the direction (b-axis) connected by TSeF (tetraselenafulvalene), and relatively high insulation was found in the c-axis direction perpendicular to the b-axis. The resistivity in the b-axis direction is larger by about 100,000,000 times than the resistivity in the c-axis direction.

The application voltage was changed to a value of 200V, 100V, 0V, −100V, and −200V, thereby, the result showed linearity.

Figure 5:
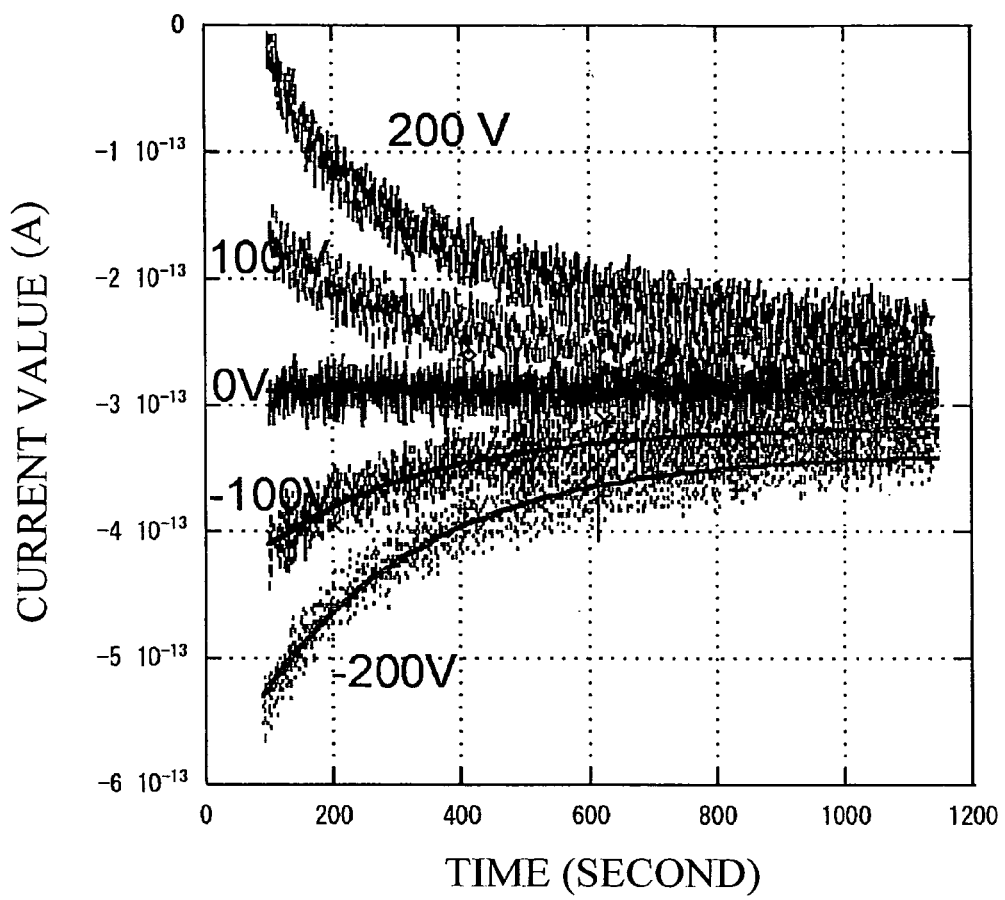
FIG. 5 shows a relation between a current value and a time of the nano wire material according to the invention.

The result of measurement is shown in FIG. 5.

INDUSTRIAL APPLICABILITY

The nano wire material according to the invention can be widely used in the field of electronic such as electronic elements. Specifically, the nano wire material can be used in semiconductors, displays, recording devices.

What is claimed is:

1. A molecular monocrystal comprising a conductive portion and an insulating portion covering the conductive portion, wherein the conductive portion comprises conductive molecules which are arranged in series, the insulating portion comprises insulating molecules, the resistivity of the insulating portion is larger by 100,000 times or more than the resistivity of the conductive portion, the conductive molecules are any one selected from the group consisting of cation radical salts, anion radical salts, organic metal complexes, and chalcogen-containing organic compounds, and the insulating molecules contain an aromatic ring and a halogen atom.

2. A molecular monocrystal comprising a conductive portion and an insulating portion covering the conductive portion, wherein the resistivity of the insulating portion is larger by 100,000 times or more than the resistivity of the conductive portion, 1 to 16 lines in which conductive molecules having a molecular weight in the range of 150 to 800 are arranged in series are arranged in parallel in the conductive portion, the insulating portion comprises insulating molecules having a molecular weight in the range of 500 to 10,000, and the molecular monocrystal is obtainable by electrolysis of a solution containing the conductive molecules and the insulating molecules.

3. A nano wire material comprising a molecular monocrystal having a high anisotropy for electrical resistivity, and having a monocrystalline supramolecular architecture which comprises a conductive portion and an insulating portion covering the conductive portion, wherein the conductive portion comprises conductive molecules which are arranged in series, the insulating portion comprises insulating molecules, and the resistivity of the insulating portion is larger by 100,000 times or more than the resistivity of the conductive portion.

4. A nano wire material comprising a molecular monocrystal having high anisotropy for electrical resistivity, wherein the monocrystal comprises a conductive portion and an insulating portion covering the conductive portion, wherein the resistivity of the insulating portion is larger by 100,000 times or more than the resistivity of the conductive portion, 1 to 16 lines in which conductive molecules having a molecular weight in the range of 150 to 800 are arranged in series are arranged in parallel in the conductive portion, the insulating portion comprises insulating molecules having a molecular weight in the range of 500 to 10,000, and the monocrystal is obtainable by electrolysis of a solution containing the conductive molecules and the insulating molecules.

5. The nano wire material according to claim 4, wherein the conductive molecules are any one selected from the group consisting of cation radical salts, anion radical salts, organic metal complexes, and chalcogen-containing organic compounds.

6. The nano wire material according to claim 3, wherein the conductive molecules are any one selected from the group consisting of cation radical salts, anion radical salts, organic metal complexes, and chalcogen-containing organic compounds, and the insulating portion contains an organic molecule.

7. The nano wire material according to claim 3, wherein the insulating molecules contain a benzene ring and a halogen atom.

8. The nano wire material according to claim 4, wherein the monocrystal has a supramolecular architecture.

9. The nano wire material according to claim 3, wherein the conductive molecules have a fulvalene skeleton.

10. The nano wire material according to claim 9, wherein the conductive molecules are tetraselenafulvalene.

11. The nano wire material according to claim 3, wherein the insulating molecules have an aromatic-series skeleton.

12. The nano wire material according to claim 11, wherein the insulating molecules are an aromatic series having an alkynyl group.

13. The nano wire material according to claim 3, wherein the insulating molecules contain a halogen atom.

14. The nano wire material according to claim 13, wherein the insulating molecules are bonded to each other with the halogen atom therebetween.

15. The nano wire material according to claim 3, wherein the insulating molecules have a twofold symmetry.

16. The nano wire material according to claim 3, wherein the nano wire material comprises two or more conductive portions and an insulating portion, and wherein the two or more conductive portions are collected to be covered with the insulating portion.

17. The nano wire material according to claim 3, wherein the nano wire material comprises a first layer comprising a conductive portion which is arranged in parallel and a second layer comprising a conductive portion which is arranged in parallel, and the second layer is stacked on the first layer so that the conductive portion of the first layer is approximately perpendicular to the conductive portion of the second layer.

18. The nano wire material according to claim 17, wherein the first layer and the second layer are stacked alternatively.

19. The nano wire material according to claim 3, wherein the resistivity of the insulating portion is larger by 10,000,000 times or more than the resistivity of the conductive portion.

20. The nano wire material according to claim 3, wherein the thickness of the insulating portion is 1.0 nm or more.

21. An electronic element comprising the nano wire material according to claim 3.

22. A method of producing the nano wire material according to claim 3, comprising forming a supramolecular architecture out of a solution containing conductive molecules and insulating molecules by the use of interaction between the molecules.

23. An electronic element comprising the nano wire material according to claim 4.

24. A method of producing the nano wire material according to claim 4, comprising forming a supramolecular architecture out of a solution containing conductive molecules and insulating molecules by the use of interaction between the molecules.

* * * * *